(12) United States Patent
Shibutani

(10) Patent No.: US 9,275,283 B2
(45) Date of Patent: Mar. 1, 2016

(54) FUNDUS IMAGE PROCESSING APPARATUS AND FUNDUS OBSERVATION APPARATUS

(75) Inventor: Masahiro Shibutani, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 497 days.

(21) Appl. No.: 13/806,326

(22) PCT Filed: Sep. 14, 2011

(86) PCT No.: PCT/JP2011/005169
§ 371 (c)(1),
(2), (4) Date: Dec. 21, 2012

(87) PCT Pub. No.: WO2012/063390
PCT Pub. Date: May 18, 2012

(65) Prior Publication Data
US 2013/0093870 A1    Apr. 18, 2013

(30) Foreign Application Priority Data

Nov. 9, 2010  (JP) ................................ 2010-250786

(51) Int. Cl.
*A61B 3/10*  (2006.01)
*A61B 3/12*  (2006.01)
*A61B 3/14*  (2006.01)
(Continued)

(52) U.S. Cl.
CPC ............ *G06K 9/00604* (2013.01); *A61B 3/102* (2013.01); *A61B 3/1225* (2013.01)

(58) Field of Classification Search
None
See application file for complete search history.

(56) References Cited

U.S. PATENT DOCUMENTS

| 6,276,798 | B1* | 8/2001 | Gil et al. ................... 351/206 |
| 6,377,349 | B1* | 4/2002 | Fercher ................... 356/497 |
| 6,549,801 | B1* | 4/2003 | Chen et al. .............. 600/425 |

(Continued)

FOREIGN PATENT DOCUMENTS

| JP | 09-276232 A | 10/1997 |
| JP | 11-325849 A | 11/1999 |

(Continued)

OTHER PUBLICATIONS

Omodaka et al., "Correlation between morphology of optic disc determined by Heidelberg Retina Tomograph II and visual function in eye with open-angle glaucoma," Clinical Ophthalmology 2010:4, pp. 765-772.*

Srinivasan et al., "Ultrahigh-Speed Optical Coherence Tomography for Three-Dimensional and En Face Imaging of the Retina and Optic Nerve Head," Investigative Ophthalmology and Visual Science, vol. 49. No. 11, Nov. 2008, pp. 5130-5110.*

(Continued)

*Primary Examiner* — Jayanti K Patel
*Assistant Examiner* — Reza Aghevli
(74) *Attorney, Agent, or Firm* — Pearne & Gordon LLP

(57) ABSTRACT

To provide the status of the cribrosa lamina of an eye of a living body as diagnostic material. A tomographic image forming part 232 of a fundus observing device 1 forms a horizontal tomographic image Wi based on a three-dimensional image V of a fundus Ef. A cribrosa-lamina region specifying part 233 specifies a cribrosa-lamina region Uj by analyzing the horizontal tomographic image Wi. A hole region specifying part 234 specifies a hole region Pk in the cribrosa-lamina region Uj by analyzing the horizontal tomographic image Wi. The distribution information generating part 235 generates distribution information representing the distribution of the hole region Pk in the cribrosa-lamina region Uj based on the specifying results of the cribrosa-lamina region Uj and the hole region Pk. This distribution information is displayed by a display 240.

8 Claims, 9 Drawing Sheets

(51) Int. Cl.
  *G01N 21/17* (2006.01)
  *G06K 9/00* (2006.01)

(56) References Cited

U.S. PATENT DOCUMENTS

| | | | |
|---|---|---|---|
| 7,290,880 B1* | 11/2007 | Yaron et al. | 351/206 |
| 7,345,770 B2 | 3/2008 | Chan et al. | |
| 7,992,999 B2* | 8/2011 | Xu et al. | 351/206 |
| 8,137,271 B2 | 3/2012 | Bille | |
| 2009/0153798 A1* | 6/2009 | Dick et al. | 351/206 |
| 2010/0160789 A1* | 6/2010 | Dilworth et al. | 600/476 |
| 2011/0091083 A1* | 4/2011 | Liu et al. | 382/128 |
| 2012/0140178 A1 | 6/2012 | Bille | |
| 2012/0143035 A1 | 6/2012 | Bille | |

FOREIGN PATENT DOCUMENTS

| | | |
|---|---|---|
| JP | 2002-139421 A | 5/2002 |
| JP | 2006-153838 A | 6/2006 |
| JP | 2007-024677 A | 2/2007 |
| JP | 2008-073099 A | 4/2008 |
| JP | 2008-259544 A | 10/2008 |
| JP | 2010-201174 A | 9/2010 |

OTHER PUBLICATIONS

Siddalingaswamy et el., "Automatic Localization and Boundary Detection of Optic Disc Using Implicit Active Contours," IEEE Int'l Jour. of Computer Application, vol. 1, No. 7, 2010, pp. 1-5.*
Akram et al., "Retinal Images: Optic Disc Localization and Detection," ICIAR 2010, Part II, LNCS 6112, 2010, pp. 40-49.*
"Three-dimensional High-speed Optical Coherence Tomography Imaging of Lamina Cribrosa in Glaucoma", Ophthalmology, 2009. vol. 116, No. 2, p. 214-222.
Kazuo Iwata, Reiko Iwata, "3D OCT-1000 de Miru Ryokunaisho Shijoban no Judanmen", Folia Japonica de Ophthalmologia Clinica, Jul. 15, 2009, vol. 2, No. 7, p. 656.
Ryo Inoue et al., "Ryokunaisho Seminar 121 Hikari Kansho Dansokei (OCT) de Miru Shijoban Kozo Henka", Journal of the Eye, Jul. 30, 2010 vol. 27, No. 7, pp. 935 to 936.
Hidetaka Maeda et al., Morphometric Features in the Lamina Cribrosa Observed by a Scanning Laser Ophthalmological Society, 1999.01, vol. 103, No. 1, pp. 48 to 55.
Tadamichi Akagi, "Hosho Kogaku Sosagata Laser Kengankyo o Mochiita Ryokunaishogan no Shijoban Kokeijo Kaiseki", Annual Meeting of Japan Glaucoma Society Shorokushu, Sep. 25, 2010 vol. 21, p. 84

* cited by examiner

FUNDUS IMAGE PROCESSING APPARATUS AND FUNDUS OBSERVATION APPARATUS

TECHNICAL FIELD

The present invention relates to a fundus image processing apparatus that processes a three-dimensional image of a fundus, and a fundus observation apparatus that forms a three-dimensional image of a fundus by using optical coherence tomography (OCT) and processes it.

BACKGROUND ART

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, devices that form images of a fundus and cornea or the like are in a practical stage.

Patent Document 1 discloses a device to which OCT is applied (referred to as an OCT apparatus). This OCT apparatus has such a configuration that: a measuring arm scans an object by a rotary deflection mirror (a Galvano mirror); a reference arm is provided with a reference mirror; and an interferometer is mounted at the outlet to analyze, by a spectrometer, the intensity of an interference light of light fluxes from the measurement arm and the reference arm. Moreover, the reference arm is configured to gradually change the light flux phase of the reference light by discontinuous values.

The OCT apparatus of Patent Document 1 uses a technique of so-called "Fourier Domain OCT." That is to say, the device irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. The technique of this type is also called Spectral Domain.

Furthermore, the OCT apparatus described in Patent Document 1 is provided with a Galvano mirror that scans with a light beam (a signal light), and is thereby configured to form an image of a desired measurement target region of the object. Because this OCT apparatus is configured to scan with the light beam only in one direction (the x-direction) orthogonal to the z-direction, an image formed by this device is a two-dimensional tomographic image in the depth direction (the z-direction) along the scanning direction (the x-direction) of the light beam.

Patent Document 2 discloses a technique of scanning with a signal light in the horizontal direction (x-direction) and the vertical direction (y-direction) to form multiple two-dimensional tomographic images in the horizontal direction, and acquiring and imaging three-dimensional tomographic information of a measured range based on the tomographic images. As the three-dimensional imaging, for example, a method of arranging and displaying multiple tomographic images in the vertical direction (referred to as stack data or the like), and a method of executing a rendering process on multiple tomographic images to form a three-dimensional image are considered.

Patent Documents 3 and 4 disclose other types of OCT devices. Patent Document 3 describes an OCT device that images the morphology of an object by sweeping the wavelength of light that is irradiated to an object, acquiring the spectral intensity distribution based on an interference light obtained by superposing the reflected lights of the light of the respective wavelengths on the reference light, and executing Fourier transform. Such an OCT device is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. In addition, before OCT was applied, a retinal camera, a slit lamp, etc. were used as devices for observing an eye (e.g., see Patent Documents 6 and 7). The retinal camera is a device that photographs the fundus by projecting illumination light onto the eye and receiving the reflected light from the fundus. The slit lamp is a device that obtains an image of the cross-section of the cornea by cutting off the light section of the cornea using slit light.

The device with OCT is superior relative to the retinal camera, etc. in that high-definition images can be obtained, further in that tomographic images and three-dimensional images can be obtained, etc.

Thus, the apparatus using OCT can be used for observation of various regions of the eye and is capable of obtaining high-definition images, and therefore, has been applied to the diagnosis of various ophthalmic disorders.

PRIOR ART DOCUMENTS

Patent Documents

[Patent Document 1]
  Japanese Unexamined Patent Application Publication No. Hei 11-325849
[Patent Document 2]
  Japanese Unexamined Patent Application Publication No. 2002-139421
[Patent Document 3]
  Japanese Unexamined Patent Application Publication No. 2007-24677
[Patent Document 4]
  Japanese Unexamined Patent Application Publication No. 2006-153838
[Patent Document 5]
  Japanese Unexamined Patent Application Publication No. 2008-73099
[Patent Document 6]
  Japanese Unexamined Patent Application Publication No. Hei 9-276232
[Patent Document 7]
  Japanese Unexamined Patent Application Publication No. 2008-259544

SUMMARY OF THE INVENTION

Problem that the Invention is to Solve

Glaucoma is regarded as one of ophthalmic disorders effectively using OCT. Glaucoma is a progressive disorder involving changes in the optic nerve and an abnormal visual field and it is thought that a fragile optic disk is the cause thereof. In the diagnosis of glaucoma, the status of the cribrosa lamina of the optic nerve (sometimes simply referred to as the cribrosa lamina) sometimes attracts attention. For example, the relation between the distribution of holes in the cribrosa lamina and glaucoma has been researched. Observation of the cribrosa lamina in the eye of a living body was almost impossible prior to the application of OCT; however, the application of OCT has made the observation of the cribrosa lamina in an eye of a living body possible.

However, with conventional OCT apparatuses, it has been difficult to show, in an effective fashion, the status of the cribrosa lamina of a living body (for example, the distribution status of the holes and their morphologies) for the purpose of diagnosis. Particularly, it has been difficult to quantitatively evaluate the status of the cribrosa lamina and show the morphology of holes of the cribrosa lamina. Accordingly, it has been difficult to use the status of the cribrosa lamina as diagnostic material.

The present invention resolves the above-mentioned problem, with the object of providing the status of the cribrosa lamina in an eye of a living body as diagnostic material.

Means for Solving the Problem

In order to achieve the aforementioned object, the first aspect of the invention is a fundus image processing apparatus for receiving and processing a three-dimensional image representing the morphology of a region of a fundus including the optic disk of an eye, comprising: a tomographic image forming part that forms a tomographic image representing the morphology of the optic disk based on the three-dimensional image; a first specifying part that analyzes the tomographic image and specifies a cribrosa-lamina region in the tomographic image; a second specifying part that analyzes the tomographic image and specifies a hole region in the cribrosa-lamina region; a generating part that generates distribution information representing the distribution, in the cribrosa-lamina region, of the hole region that are specified by the second specifying part; and a display that displays the distribution information.

Furthermore, the second aspect of the invention is characterized in that the distribution information includes at least one of a statistical value based on the sizes of multiple connected regions included in the hole region and the area ratio between the hole region and the cribrosa-lamina region.

Furthermore, the third aspect of the invention is characterized in that the display shows the tomographic image so that the hole region, an image region in the cribrosa-lamina region other than the hole region, and an image region in the tomographic image other than the cribrosa-lamina region are shown in respectively different display modes.

Furthermore, the fourth aspect of the invention is characterized in that: the tomographic image forming part forms, as the tomographic image, multiple horizontal tomographic images that are perpendicular to the depth direction of the optic disk and have different depth positions; the first specifying part specifies the cribrosa-lamina region for each of the multiple horizontal tomographic images; the second specifying part specifies the hole region for each of the multiple horizontal tomographic images; and the generating part obtains a horizontal distribution of the hole region in the cribrosa-lamina region at each of the different depth positions based on the specifying results of the cribrosa-lamina region and the specifying results of the hole region, and further obtains, as the distribution information, changes of the distribution of the hole region in the depth direction based on the horizontal distributions at the different depth positions.

Furthermore, the fifth aspect of the invention is characterized in that the fundus image processing apparatus comprises a three-dimensional image forming part that forms a new three-dimensional image based on the multiple horizontal tomographic images from which the distribution information representing the changes of the distribution is obtained.

Furthermore, the sixth aspect of the invention is characterized in that: the tomographic image forming part forms a vertical tomographic image along the depth direction based on the new three-dimensional image; and the display shows the vertical tomographic image.

Furthermore, the seventh aspect of the invention is characterized in that the display shows the vertical tomographic image while changing the display mode of the hole region based on the distribution information.

Furthermore, the eighth aspect of the invention is characterized in that: the tomographic image forming part forms a vertical tomographic image along the depth direction of the optic disk based on the three-dimensional image; the first specifying part specifies the cribrosa-lamina region in the vertical tomographic image; the second specifying part specifies the hole region in the vertical tomographic image; the generating part obtains, as the distribution information, the vertical distribution of the hole region in the cribrosa-lamina region based on the specifying result of the cribrosa-lamina region and the specifying result of the hole region.

Furthermore, the ninth aspect of the invention is characterized in that the first specifying part specifies a disk region corresponding to the optic disk and a blood-vessel region corresponding to a blood vessel in the tomographic image based on a pixel value of the tomographic image, and specifies the region obtained by removing the blood-vessel region from the disk region as the cribrosa-lamina region.

Furthermore, the tenth aspect of the invention is characterized in that: the tomographic image comprises a brightness image having multiple pixels representing brightness values arrayed in a matrix; and the second specifying part creates a first graph to relate the position of the pixel in each pixel line in the vertical direction and/or the horizontal direction in the tomographic image with the brightness value, obtains a maximal envelope connecting the local maximums of the first graph and a minimal envelope connecting the local minimums of the first graph, obtains a second graph that internally divides the interval between the maximal envelope and the minimal envelope in the direction of a coordinate axis representing the brightness value of the first graph at a predetermined ratio, and specifies a pixel with a smaller brightness value than that of the second graph as a pixel of the hole region.

Furthermore, the eleventh aspect of the invention is a fundus observation apparatus comprising: an optical system that splits low-coherence light into signal light and reference light, generates interference light by interfering the signal light that has passed through a fundus of an eye and the reference light that has passed through a reference optical path, and detects the interference light; a forming part that forms a three-dimensional image representing the morphology of a region of the fundus including an optic disk based on the detection result of the interference light; a tomographic image forming part that forms a tomographic image representing the morphology of the optic disk based on the three-dimensional image; a first specifying part that analyzes the tomographic image and specifies a cribrosa-lamina region in the tomographic image; a second specifying part that analyzes the tomographic image and specifies a hole region in the cribrosa-lamina region; a generating part that generates distribution information representing the distribution, in the cribrosa-lamina region, of the hole regions that are specified by the second specifying part; and a display that displays the distribution information.

Effect of the Invention

According to the present invention, it is possible to specify a cribrosa-lamina region in a tomographic image showing the morphology of an optic disk, specify a hole region in the cribrosa-lamina region, generate distribution information showing the distribution of the hole region in the cribrosa-lamina region, and display this distribution information. As a result, it is possible to provide the distribution information reflecting the status of the cribrosa lamina of an eye of a living body as diagnostic material.

MODE FOR CARRYING OUT THE INVENTION

Examples of embodiments of a fundus image processing apparatus and a fundus observation apparatus according to the present invention will be described in detail with reference to the drawings. The fundus image processing apparatus according to the present invention receives input of a three-dimensional image of a fundus and processes it. Furthermore, the fundus observation apparatus according to the present invention forms a tomographic image and a three-dimensional image of a fundus by using OCT. The fundus observation apparatus according to the present invention includes the fundus image processing apparatus. It should be noted that an image obtained by OCT is sometimes referred to as an OCT image. Furthermore, a measuring action for forming an OCT image is sometimes referred to as an OCT measurement.

According to the following embodiments, the configuration employing a Fourier Domain OCT will be described in detail. Particularly, in the following embodiments, a fundus observation apparatus capable of obtaining both a fundus OCT image and a fundus image is considered as well as the apparatus disclosed in Patent Document 5. Further, even when other types of OCT are used, by utilizing similar configuration as that which follows, it is possible to obtain the same operation and effects.

[Configuration]

Figure 1:
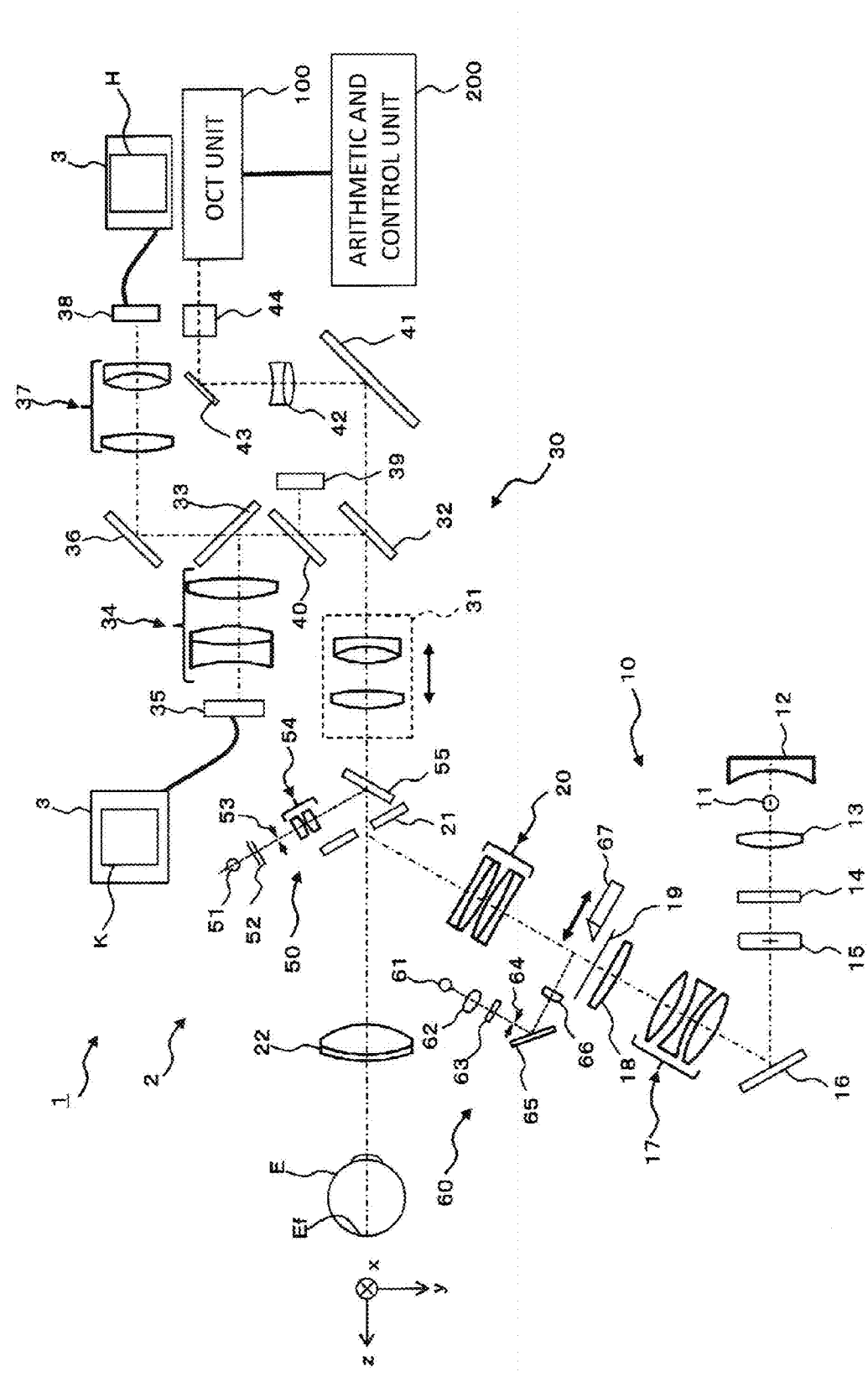
[FIG. 1] A schematic diagram showing an example of a configuration of an embodiment of a fundus observation apparatus according to the present invention.
Figure 2:
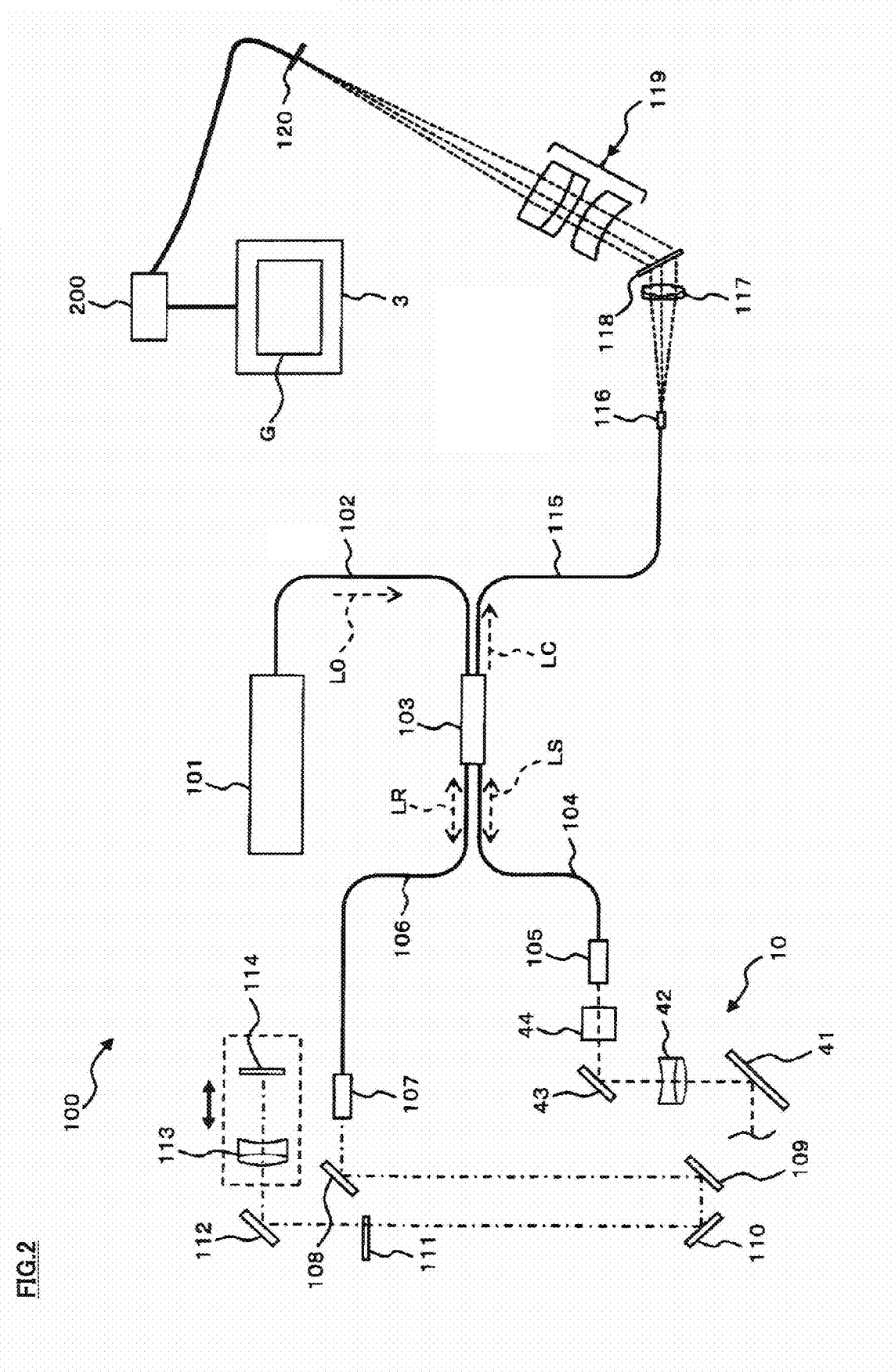
[FIG. 2] A schematic diagram showing an example of a configuration of an embodiment of a fundus observation apparatus according to the present invention.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit shown in FIG. 1 is provided with an optical system for forming a 2-dimensional image (fundus image) representing the surface morphology of the fundus Ef of an eye E. Fundus images include observation images, photographed images, etc. The observation image is, for example, a monochrome moving image formed at a pre-scribed frame rate using near-infrared light. The photographed image is, for example, a color image captured by flashing visible light. It should be noted that the retinal camera unit 2 may also be configured so as to be capable of capturing other types of images such as a fluorescent angiography image, an indocyanine green fluorescent image, and an autofluorescent image.

Fundus images to be used for the present invention are mainly photographed images. Fundus images are not limited to color images and may be arbitrary two-dimensional image that depicts the surface morphology of the fundus such as a fluorescence image or a stereoscopic fundus image. Further, stereoscopic fundus images generally comprise two fundus images with different angles of view; however, recently, a technique of stereoscopically viewing one fundus image is also being employed.

The retinal camera unit 2 is provided with a chin rest and a forehead placement for retaining the face of the subject. Moreover, the retinal camera unit 2 is provided with an illumination optical system 10 and an imaging optical system 30. The illumination optical system 10 irradiates an illumination light to the fundus Ef. The imaging optical system 30 guides a fundus reflected light of the illumination light to imaging devices (CCD image sensors 35, 38). Moreover, the imaging optical system 30 guides a signal light LS coming from the OCT unit 100 to the fundus Ef, and guides the signal light propagated through the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near infrared after passing through a visible cut filter 14 via a condenser lens 13. Furthermore, the observation illumination light is once converged near an imaging light source 15, reflected by a mirror 16, and passes through relay lenses 17, 18, diaphragm 19, and relay lens 20. Then, the observation illumination light is reflected on the peripheral part (the surrounding region of an aperture part) of an aperture mirror 21 and illuminates the fundus Ef via an object lens 22.

The fundus reflection light of the observation illumination light is refracted by the object lens 22, passes through the aperture part formed in the center region of the aperture mirror 21, passes through a dichroic mirror 55 and, travels through a focusing lens 31, and is reflected by a dichroic mirror 32. Furthermore, the fundus reflection light passes through a half-mirror 40 and forms an image on the light receiving surface of the CCD image sensor 35 by a condenser lens 34 after being reflected by a dichroic mirror 33. The CCD image sensor 35 detects, for example, the fundus reflection light at a prescribed frame rate. An image (observation image) K based on the fundus reflection light detected by the CCD image sensor 35 is displayed on a display device 3.

The imaging light source 15 consists of, for example, a xenon lamp. The light (imaging illumination light) output from the imaging light source 15 is irradiated to the fundus Ef via a route that is similar to the observation illumination light. The fundus reflection light of the imaging illumination light is guided to the dichroic mirror 33 via the same route as that of the observation illumination light, passes through the dichroic mirror 33, and forms an image on the light receiving surface of the CCD image sensor 38 by a condenser lens 37 after being reflected by a mirror 36. An image (photographed image) H based on the fundus reflection light detected by the CCD image sensor 38 is displayed on the display device 3. It should be noted that the display device 3 for displaying an observation image K and the display device 3 for displaying a photographed image H may be the same or different.

An LCD (Liquid Crystal Display) 39 displays a fixation target or a visual target for measuring eyesight. The fixation target is a visual target for fixing the eye E, and is used when photographing a fundus or performing an OCT measurement.

Part of the light output from the LCD 39 is reflected by a half-mirror 40, reflected by the dichroic mirror 32, passes through the aperture part of the aperture mirror 21 via the focusing lens 31 as well as a dichroic mirror 55, is refracted by the object lens 22 and projected to the fundus Ef.

By changing a display position of the fixation target on the screen of the LCD 39, it is possible to change a fixation position of the eye E. As the fixation position of the eye E, there are a position for acquiring an image centered on the macula of the fundus Ef, a position for acquiring an image centered on the optic papilla, a position for acquiring an image centered on the fundus center between the macula and the optic papilla, and so on, for example, as in conventional retinal cameras.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from the LED (Light Emitting Diode) 51 of the alignment optical system 50 is reflected by the dichroic mirror 55 via diaphragms 52, 53 and a relay lens 54, passes through the aperture part of the aperture mirror 21, and is projected onto the cornea of the eye E by the object lens 22.

Part of cornea reflection light of the alignment light is transmitted through the dichroic mirror 55 via the object lens 22 and the aperture part, passes through the focusing lens 31, is reflected by the dichroic mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 along with the observation image K. A user conducts alignment by an operation that is the same as conventional retinal cameras. It should be noted that alignment may be performed, by an arithmetic and control unit 200, as a result of analyzing the position of the alignment target and moving the optical system.

In order to conduct focus adjustment, the reflection surface of a reflection rod 67 is provided in a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light is reflected at the aperture mirror 21 via the relay lens 20 and an image is formed on the fundus Ef by the object lens 22.

The fundus reflection light of the focus light passes through the same route as the cornea reflection light of the alignment light and is detected by the CCD image sensor 35. A light (split target) captured by the CCD image sensor 35 is displayed on the display device 3 along with an observation image K. The arithmetic and control unit 200, as in the past, analyzes the position of the split target, and moves the focusing lens 31 and the focus optical system 60 for focusing. It should be noted that focusing may be performed manually while visually recognizing the split target.

An optical path including a mirror 41, collimator lens 42, and Galvano mirrors 43, 44 is provided behind the dichroic mirror 32. The optical path is connected to the OCT unit 100.

The Galvano mirror 44 performs scanning with a signal light LS from the OCT unit 100 in the x-direction. The Galvano mirror 43 performs scanning with a signal light LS in the y-direction. Scanning may be performed with the signal light LS in an arbitrary direction in the xy-plane due to the two Galvano mirrors 43 and 44.

[OCT Unit]

The OCT unit 100 is provided with an optical system for obtaining an OCT image of the fundus Ef (see FIG. 2). The optical system has a similar configuration to a conventional Fourier-Domain-type OCT device. That is to say, the optical system is configured to split low-coherence light into signal light and reference light, generate interference light by interfering the signal light that has passed through the fundus Ef and the reference light that has passed through a reference optical path, and detect the spectral components of the interference light. This detection result (detection signal) is transmitted to the arithmetic and control unit 200.

A light source unit 101 outputs a broadband low-coherence light L0. The low-coherence light L0, for example, includes near-infrared wavelength bands (about 800-900 nm) and has a coherence length of about tens of micrometer. Moreover, it is possible to use, as the low-coherence light L0, near-infrared light having wavelength bands that are impossible to be detected by human eyes, for example, infrared light having the center wavelength of about 1050-1060 nm.

The light source unit 101 is configured to include light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into signal light LS and reference light LR. It should be noted that the fiber coupler 103 acts both as a means to split light (splitter) as well as a means to synthesize light (coupler), but herein the same is conventionally referred to as a "fiber coupler."

The signal light LS is guided by the optical fiber 104 and becomes a parallel light flux by a collimator lens unit 105. Furthermore, the signal light LS is reflected by Galvano mirrors 44 and 43, converged by the collimator lens 42, reflected by the mirror 41, transmitted through a dichroic mirror 32, and irradiated to the fundus Ef after passing through a route that is the same as the light from the LCD 39. The signal light LS is scattered and reflected at the fundus Ef. The scattered light and the reflection light are sometimes all together referred to as the fundus reflection light of the signal light LS. The fundus reflection light of the signal light LS progresses along the same route in the reverse direction and is guided to the fiber coupler 103.

The reference light LR is guided by an optical fiber 106 and becomes a parallel light flux by a collimator lens unit 107. Furthermore, the reference light LR is reflected by mirrors 108, 109, 110, dimmed by an ND (Neutral Density) filter 111, and reflected by a mirror 112, with the image formed on a reflection surface of a reference mirror 114 by a collimator lens 113. The reference light LR reflected by the reference mirror 114 progresses along the same route in the reverse direction and is guided to the fiber coupler 103. It should be noted that an optical element for dispersion compensation (pair prism, etc.) and/or an optical element for polarization correction (wave plate, etc.) may also be provided for the optical path (reference optical path) of the reference light LR.

The fiber coupler 103 superposes the fundus reflection light of the signal light LS and the reference light LR reflected by the reference mirror 114. Interference light LC thus generated is guided by an optical fiber 115 and output from an exit end 116. Furthermore, the interference light LC is converted to a parallel light flux by a collimator lens 117, spectrally divided (spectrally decomposed) by a diffraction grating 118, converged by the convergence lens 119, and projected onto the light receiving surface of a CCD image sensor 120. The diffraction grating 118 shown in FIG. 2 is of the transmission type, but the reflection type can also be used.

The CCD image sensor 120 is for example a line sensor, and detects the respective spectral components of the spectrally decomposed interference light LC and converts the components into electric charges. The CCD image sensor 120 accumulates these electric charges and generates a detection signal. Furthermore, the CCD image sensor 120 transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, can be used.

[Arithmetic and Control Unit]

A configuration of the arithmetic and control unit 200 will be described. The arithmetic and control unit 200 analyzes the detection signals inputted from the CCD image sensor 120, and forms an OCT image of the fundus Ef. An arithmetic process for this is the same as that of a conventional Fourier-Domain-type OCT device.

Further, the arithmetic and control unit 200 controls each part of the retinal camera unit 2, the display device 3 and the OCT unit 100. For example, the arithmetic and control unit 200 causes an OCT image such as a tomographic image G (see FIG. 2) of the fundus Ef to be displayed on the display device 3.

Further, as control of the retinal camera unit 2, the arithmetic and control unit 200 executes: control of action of the observation light source 101, the imaging light source 103 and LED's 51 and 61; control of action of the LCD 39; control of movement of the focusing lens 31; control of movement of the reflection rod 67; control of movement of the focus optical system 60; control of action of the respective Galvano mirrors 43 and 44; and so on.

Further, as control of the OCT unit 100, the arithmetic and control unit 200 executes: control of action of the light source unit 101; control of movement of the reference mirror 114 and the collimator lens 113; control of action of the CCD image sensor 120; and so on.

The arithmetic and control unit 200 includes a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with a circuit board dedicated for forming OCT images based on detection signals from the CCD image sensor 120. Moreover, the arithmetic and control unit 200 may be provided with operation devices (input devices) such as a keyboard and a mouse, and/or display devices such as LCD.

The retinal camera unit 2, display device 3, OCT unit 100, and arithmetic and control unit 200 may be integrally configured (that is, within a single case), or configured as separate bodies.

[Control System]

Figure 3:
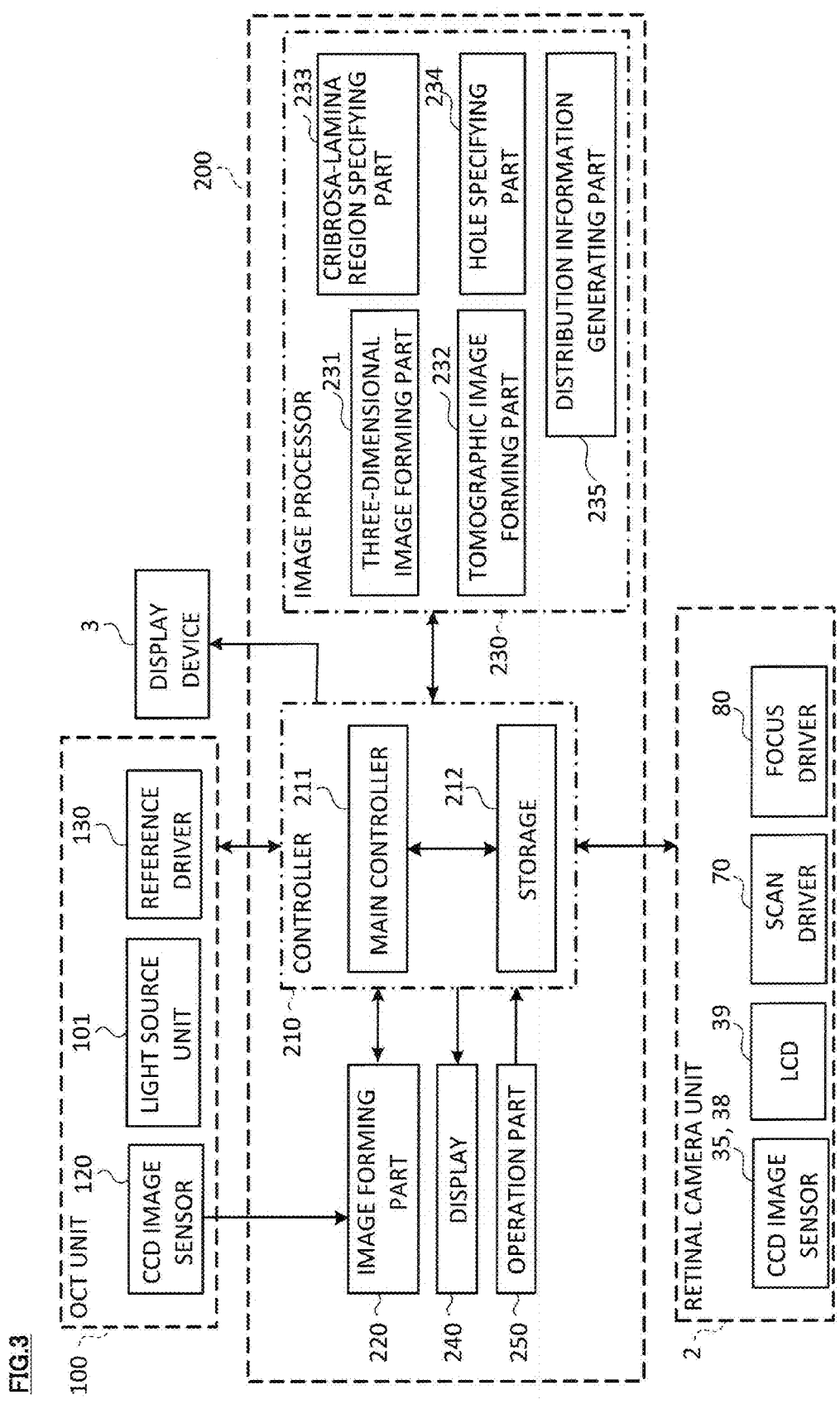
[FIG. 3] A schematic block diagram showing an example of a configuration of an embodiment of a fundus observation apparatus according to the present invention.

A configuration of a control system of the fundus observation apparatus 1 will be described with reference to FIG. 3.

(Controller)

The control system of the fundus observation apparatus has a configuration centered on a controller 210 of the arithmetic and control unit 200. The controller 210 includes, for example, the aforementioned microprocessor, RAM, ROM, hard disk drive, and communication interface. The controller 210 is provided with a main controller 211 and storage 212.

(Main Controller)

The main controller 211 performs the aforementioned various kinds of control. Specifically, the main controller 211 controls a scan driver 70 as well as a focus driver 80 of the retinal camera unit 2, and further controls the light source unit 101 and a reference driver 130 of the OCT unit 100.

The scan driver 70 is configured, for example, including a servo motor and independently changes the facing direction of the Galvano mirrors 43 and 44. The focus driver 80 is configured, for example, including a pulse motor and moves the focusing lens 31 in the optical axis direction. Thereby, the focus position of light towards the fundus Ef is changed. The reference driver 130 is configured, for example, including a pulse motor and integrally moves the collimator lens 113 as well as the reference mirror 114 along the travelling direction of the reference light LR.

The main controller 211 executes a process of writing data into the storage 212, and a process of reading out the data from the storage 212.

(Storage)

The storage 212 stores various kinds of data. The data stored in the storage 212 is, for example, image data of OCT images, image data of fundus images, and eye information. The eye information includes information on the eye, for example, information on a subject such as a patient ID and a name, information on identification of left eye or right eye, and so on.

(Image Forming Part)

An image forming part 220 forms image data of a tomographic image of the fundus Ef based on the detection signals from the CCD image sensor 120. Like the conventional Fourier-Domain OCT, this process includes processes such as noise elimination (noise reduction), filtering, FFT (Fast Fourier Transform) and logarithmic transformation.

The image forming part 220 includes, for example, the aforementioned circuit board and communication interface. It should be noted that "image data" and the "image" presented based on the image data may be identified with each other in this specification.

(Image Processor)

An image processor 230 executes various image processing and analysis on images formed by the image forming part 220. For example, the image processor 230 executes various correction processes such as luminance correction and dispersion correction of images. Further, a specific example of processing executed by the image processor 230 is discussed in explanation on motions.

(Three-Dimensional Image Forming Part)

Three-dimensional image forming part 231 executes known image processing such as an interpolation process of interpolating pixels between tomographic images, thereby forming image data of a three-dimensional image of the fundus Ef. The image forming part 220 and the three-dimensional image forming part 231 are regarded as an example of "forming part" of the present invention.

Image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as the display 240, this pseudo three-dimensional image is displayed.

Further, it is also possible to form stack data of multiple tomographic images as the image data of a three-dimensional image. Stack data is image data obtained by three-dimensionally arranging multiple tomographic images obtained along multiple scanning lines, based on the positional relation of the scanning lines. That is to say, stack data is image data obtained by expressing multiple tomographic images defined by originally individual two-dimensional coordinate systems by a three-dimensional coordinate system (namely, embedding into a three-dimensional space).

The image processing processor 230 is further provided with a tomographic image forming part 232, a cribrosa-lamina region specifying part 233, a hole region specifying part 234, and a distribution information generating part 235. "The fundus image processing apparatus" of the present invention comprises a computer including the image processing processor 230 and the display 240. Hereinafter, these respective parts will be described.

(Tomographic Image Forming Part)

The tomographic image forming part 232 forms a tomographic image representing the morphology of an optic disk of a fundus Ef based on a three-dimensional image formed by the three-dimensional image forming part 231. This processing is MPR (Multi-Planar Reconstruction) to volume data, for example. A specific example of processing to be carried out by the tomographic image forming part 232 may include a method of obtaining a voxel value for each voxel located on a slice surface set to the volume data as a three-dimensional image, obtaining a pixel group having pixel values based on these voxel values, and forming a two-dimensional image (a tomographic image) by arraying this pixel group. With respect to stack data, a tomographic image can be formed in a similar fashion.

An example of a method of setting a slice surface will be described. An example of manual setting may include a method of rendering and displaying the three-dimensional image, and setting a slice surface to this displayed image by a user. On the other hand, an example of automatic setting may include a method of detecting a specific region (for example, an image region corresponding to an optic disk) in the three-dimensional image and the tomographic image, and setting a slice surface based on this specific region. The tomographic image forming part 232 is regarded as an example of "the tomographic image forming part" of the present invention.

(Cribrosa-Lamina Region Specifying Part)

The cribrosa-lamina region specifying part 233 specifies the cribrosa-lamina region in a tomographic image by analyzing the tomographic image formed by the tomographic image forming part 232. The cribrosa-lamina region specifying part 233 is an example of "a first specifying part" of the present invention. The cribrosa-lamina region means an image region corresponding to a cribrosa lamina that is one of the organizations constituting a fundus Ef.

An example of processing to be carried out by the cribrosa-lamina region specifying part 233 will be described. At first, the cribrosa-lamina region specifying part 233 specifies a disk region corresponding to an optic disk in the tomographic image based on the pixel value (generally speaking, the brightness value) of the tomographic image. In addition, the cribrosa-lamina region specifying part 233 specifies a blood-vessel region corresponding to a blood vessel in the tomographic image. As an example of these specifying processing, threshold value processing to the pixel value is applied. Further, the cribrosa-lamina region specifying part 233 specifies a region obtained by removing this blood-vessel region from this disk region to define this specified region as a cribrosa-lamina region. The cribrosa-lamina region of this embodiment refers to an image region corresponding to the cribrosa lamina in the optic disk; however, this may include the cribrosa lamina outside of the optic region.

Further, in the case that the above-described specifying processing cannot be preferably performed because the image quality of a tomographic image formed by the tomographic image forming part 232 is too low, it is desirable to improve the image quality by applying image processing to the tomographic image in advance. This image processing may include smoothing processing to smooth the outline of the image, processing to enlarge a dynamic range of the image, and unsharp masking processing to emphasize the outline of the image or the like. By performing the above-described specifying processing after applying these image processes, it is possible to improve the degree of precision and the degree of certainty of the processing for specifying a disk region, a blood-vessel region, and further, a hole region to be described later.

(Hole Region Specifying Part)

The hole region specifying part 234 specifies a hole region in the cribrosa-lamina region by analyzing a tomographic image formed by the tomographic image forming part 232. The hole region specifying part 234 is regarded as an example of "a second specifying part" of the present invention.

The hole region is an image region corresponding to a hole formed on the cribrosa lamina. The hole have a three-dimensional structure in which the depth direction (z-direction) of the fundus Ef is substantially the longitudinal direction, and is so called because its xy-section appears as if a hole has opened on the cribrosa lamina.

An example of processing to be performed by the hole region specifying part 234 will be described. Further, it is defined that the tomographic image of the present embodiment is a brightness image having multiple pixels representing a brightness value arrayed in a matrix. At first, for a pixel line (group of pixels arranged in a line) in a tomographic image, the hole region specifying part 234 creates a graph to relate the position with the brightness value for each pixel included in this pixel line. This graph is referred to as a brightness distribution graph. The brightness distribution graph is defined by a coordinate system with the pixel position on the horizontal axis and the brightness value on the vertical axis. An example of the pixel line and the brightness distribution graph will be described later. The brightness distribution graph is an example of "the first graph" of the present invention.

The pixel line may be formed in an arbitrary direction; however, for designing the apparatus, it is easy to adopt the horizontal direction or the vertical direction in a frame with a tomographic image depicted. As an example, the tomographic image (horizontal tomographic image) on a slice surface in parallel with the xy-face depicts the morphology of the xy-section of the cribrosa lamina at a predetermined depth position (z-coordinate position), while the hole region specifying part 234 sets a pixel line in the x-direction (horizontal direction) or the y-direction (vertical direction) to this horizontal tomographic image. Further, the direction of setting the pixel line of the horizontal tomographic image is not limited to these directions, and the pixel line may be in an arbitrary direction on the xy-plane. The direction of setting the pixel line may be set manually by a user, or the direction determined in advance may be set automatically.

After obtaining the brightness distribution graph, the hole region specifying part 234 obtains the maximal envelope connecting the local maximums of this brightness distribution graph and the minimal envelope connecting the local minimums of this brightness distribution graph. An example of this processing may include a method of obtaining maxima and minima of the brightness distribution graph by using differentiation, determining whether each value is a local maximum or a local minimum, deriving a curve passing through the obtained local maximums to obtain a maximal envelope, and deriving a curve passing through the local minimums to obtain a minimal envelope.

Subsequently, the hole region specifying part 234 obtains a graph that internally divides, at a predetermined ratio, the interval between the maximal envelope and the minimal envelope in the direction of the vertical axis (a coordinate axis representing the brightness value) direction in the brightness distribution graph. This graph is referred to as a threshold graph. The internally dividing ratio for obtaining the threshold graph may be decided manually or automatically taking into consideration the brightness distribution graph and the envelopes, or the value set in advance may be automatically applied. This internally dividing ratio is set at 1:2 in the direction from the minimum envelope to the maximal envelope, for example. In this case, the hole region specifying part 234 obtains the threshold graph by calculating the difference between the brightness value of the maximal envelope and that of the minimum envelope with respect to each point on the horizontal axis (the coordinate axis representing the position of a pixel) and adding one third of this difference to the brightness value of each point of the minimum envelope.

Next, the hole region specifying part 234 specifies a pixel having a smaller brightness value than that of the threshold graph and defines this specified pixel as the component pixel of the hole region. Sometimes this processing may be carried out several times for each pixel. In this case, the hole region specifying part 234 specifies a pixel that is a candidate for the component pixel of the hole region from the processing results in each direction and makes a final decision by combining the processing results in multiple directions for each pixel. As an example, the hole region specifying part 234 determines whether or not a pixel value is a candidate for a component pixel of the hole region both vertically and horizontally and defines component pixels of the hole region only with pixels that are determined as a candidate in both directions.

The hole region specifying part 234 specifies the component pixel of the hole region in each pixel line by applying the above processing to each of multiple pixel lines in the tomographic image. Then, the image region consisted of the pixels thus specified is regarded as the hole region.

All of the multiple pixel lines may be in the identical direction, or the multiple pixel lines may include ones in different directions. As an example of the former case, it is possible to divide all the pixels configuring the tomographic image into multiple pixel lines in the identical direction (for example, horizontal direction in the frame), and apply the above processing for each pixel line.

In addition, as an example of the latter case, it is possible to divide all the pixels configuring the tomographic image into multiple pixel lines in the horizontal direction (referred to as horizontal pixel lines) and apply the above processing to each horizontal pixel line, and divide all the pixels into the multiple pixel lines in the vertical direction (referred to as vertical pixel lines) and apply the above processing to each vertical pixel line. In this example, for each pixel configuring the tomographic image, the processing for determining whether or not this pixel is a component pixel of the hole region is performed twice, namely, in the horizontal and vertical directions. In this case, the hole region may be consisted by nothing but pixels that are determined as a candidate for the component pixel of the hole region both in the horizontal and vertical directions. On the other hand, the hole region may be configured by pixels that are determined as a component pixel of the hole region in at least one of the horizontal and vertical directions.

(Distribution Information Generating Part)

The distribution information generating part 235 generates distribution information representing the distribution of the hole region in the cribrosa-lamina region based on the cribrosa-lamina region specified by the cribrosa-lamina region specifying part 233 and the hole region specified by the hole region specifying part 234. The distribution information generating part 235 is one example of "a generating part" of the present invention.

An example of the distribution information will be described. As a first example, it is possible to obtain a statistical value based on the sizes of multiple connected regions included in the hole region as the distribution information. As described above, the hole region refers to image regions corresponding to many holes opened on the cribrosa laminate. Therefore, the hole region is a set of the connected region corresponding to each hole region. Here, the connected region means image regions having "connectivity" in mathematics. The distribution information generating part 235 obtains the size (an area or the like) of each connected region by, for example, counting the number of pixels in each connected region. In this case, a factor influencing the relation between the real size and the size of the tomographic image (magnification of an apparatus optical system, and a spherical diopter power, an astigmatic diopter power and an axial length of an eyeball system or the like) may be considered. Subsequently, the distribution information generating part 235 calculates a predetermined statistical value by applying statistical processing to the sizes of the multiple connected regions. The statistical value means the value capable of being obtained by applying statistical processing to a sample. Examples of the statistical value include an average value, a standard variation, dispersion, a maximum value, a minimum value, a median, and a mode or the like.

As a second example, it is possible to obtain an area ratio of the hole region for the cribrosa-lamina region as the distribution information. The area ratio can be obtained by, for example, counting the number of pixels in the cribrosa-lamina region and the number of pixels in the hole region, respectively, and dividing the latter by the former.

The distribution information is not limited to the above example and any mode is available if it is information representing the distribution of the hole regions in the cribrosa-lamina region. In addition, the distribution information is not limited to information representing the distribution of the hole regions in one slice surface and it may be information representing changes in the position of the distribution based on the distribution of the hole regions in multiple slice surfaces as the operation example to be described later, for example.

The image processor 230 that functions as above includes, for example, the aforementioned microprocessor, RAM, ROM, hard disk drive, circuit board, and so on. A computer program that causes the microprocessor to perform the above functions is stored in the storage device such as the hard disk drive in advance.

(Display and Operation Part)

The display 240 is configured including a display device of the aforementioned arithmetic and control unit 200. The display 240 is an example of the "display" of the present invention. The operation part 250 is configured including an operation device of the aforementioned arithmetic and control unit 200. The operation part 250 may also include various kinds of buttons or keys provided with the case of the fundus observation apparatus 1 or its outside. For example, if the retinal camera unit 2 has a case that is the same as conventional retinal cameras, a joy stick, operation panel, etc. provided with the case may also be included in the operation part 250. Furthermore, the display 240 may also include various display devices such as a touch panel monitor, etc. provided with the case of the retinal camera unit 2.

The display 240 and the operation part 250 do not need to be composed as separate devices. For example, like a touch panel LCD, a device in which the display function and the operation function are integrated can be used.

[Scan with Signal Light and OCT Image]

A scan with the signal light LS and an OCT image will be described.

The scan aspect of the signal light LS by the fundus observation apparatus 1 is, for example, a horizontal scan, vertical scan, cruciform scan, radial scan, circular scan, concentric scan, and helical scan. These scan aspects are selectively used as necessary in consideration of an observation site of the fundus, an analysis target (the retinal thickness or the like), a time required to scan, the accuracy of a scan, and so on.

A horizontal scan is a scan with the signal light LS in the horizontal direction (x-direction). The horizontal scan includes an aspect of scanning with the signal light LS along multiple scanning lines extending in the horizontal direction arranged in the vertical direction (y-direction). In this aspect, it is possible to set any interval between scanning lines. By setting the interval between adjacent scanning lines to be sufficiently narrow, it is possible to form the aforementioned three-dimensional image (three-dimensional scan). A vertical scan is also performed in a similar manner. In this embodiment, the three-dimensional scan is applied.

A cruciform scan is a scan with the signal light LS along a cross-shape trajectory formed by two linear trajectories (line trajectories) orthogonal to each other. A radial scan is a scan with the signal light LS along a radial trajectory formed by multiple line trajectories arranged at predetermined angles. The cruciform scan is an example of the radial scan.

A circular scan is a scan with the signal light LS along a circular trajectory. A concentric scan is a scan with the signal light LS along multiple circular trajectories arranged concentrically around a predetermined center position. The circular scan is an example of the concentric scan. A helical scan is a scan with the signal light LS along a helical trajectory while making the turning radius gradually smaller (or greater).

Because the Galvano mirrors 43 and 44 are configured to scan the signal light LS in the directions orthogonal to each other, they are capable of scanning with the signal light LS in the x-direction and the y-direction independently. Moreover, it is possible to scan with the signal light LS along an arbitrary trajectory on the xy-plane by simultaneously controlling the directions of the Galvano mirrors 43 and 44. Thus, it is possible to realize various types of scan aspects as described above.

By scanning the signal light LS in the mode described above, it is possible to form tomographic images of the depth direction (z-direction) of the fundus along scanning lines (scan trajectory). Moreover, in a case that the interval between scanning lines is narrow, it is possible to form the aforementioned three-dimensional image.

A region on the fundus Ef subjected to scanning by the signal light LS as above, that is a region on the fundus Ef subjected to OCT measurement, is referred to as a scanning region. A scanning region in three-dimensional scanning is a rectangular-shaped region in which multiple horizontal scans are arranged. Furthermore, a scanning region in a concentric circular scan is a disc-shaped region surrounded by the trajectories of a circular scan of a maximum diameter. Moreover, the scanning region in a radial scan is a disc-shaped (or polygonal-shaped) region linking end positions of scanning lines.

[Operation]

Figure 4:
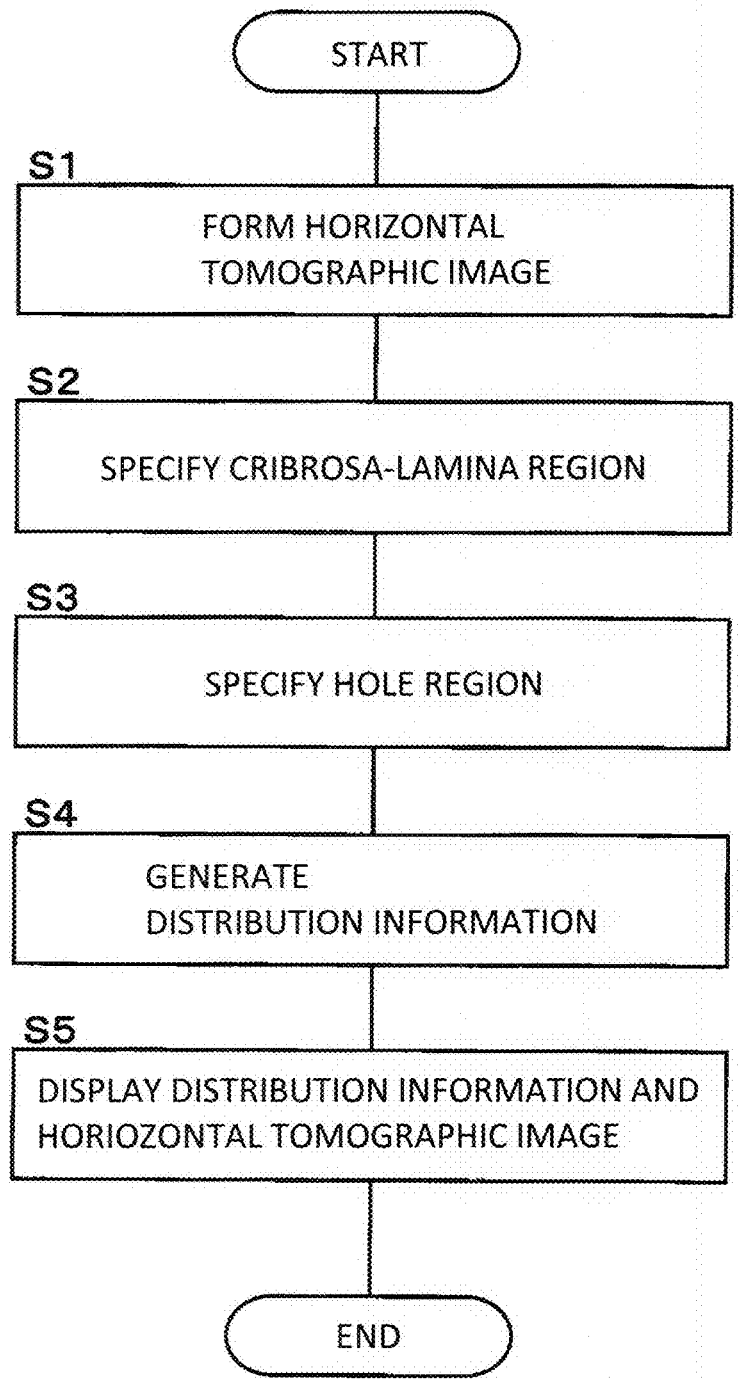
[FIG. 4] A flowchart showing an action of an embodiment of a fundus observation apparatus according to the present invention.

The operation of a fundus observation apparatus 1 will be described. The flowchart shown in FIG. 4 illustrates an example of the operation of the fundus observation apparatus 1. Further, it is assumed that a three-dimensional image V of a fundus Ef including an optic disk region T has already been formed (refer to FIG. 5).

(S1)

Figure 5:
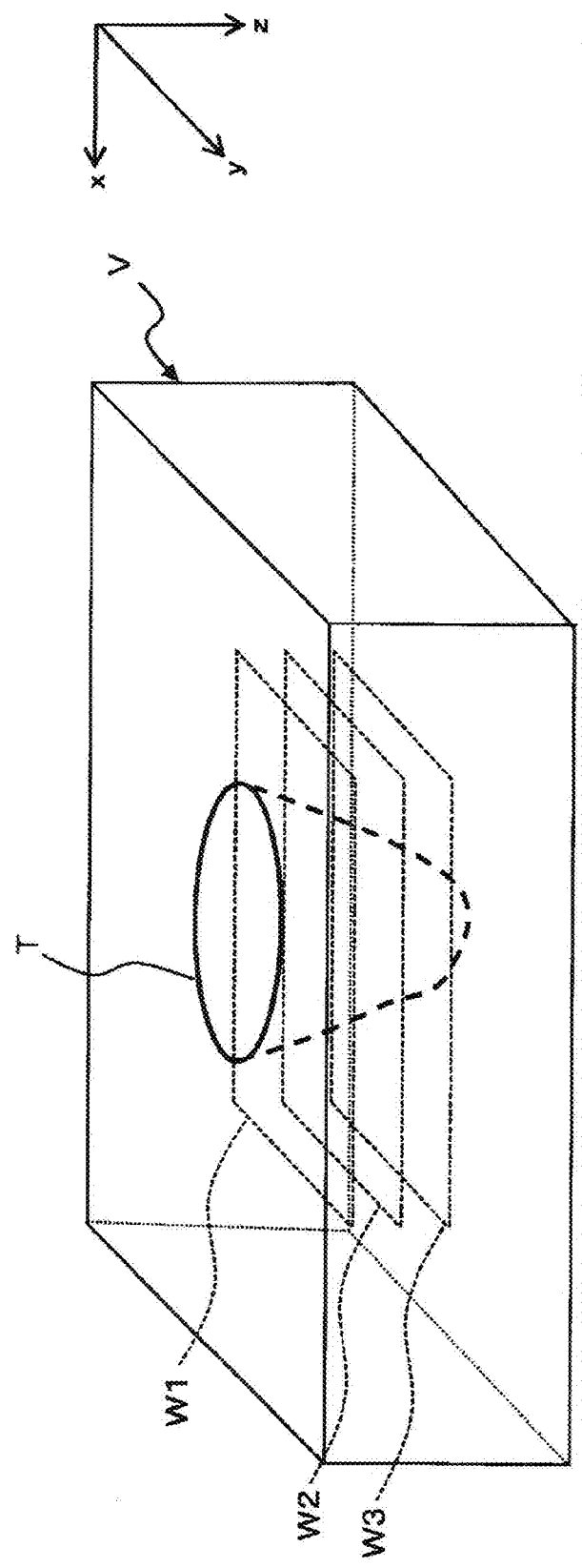
[FIG. 5] A schematic diagram for explaining processing executed by an embodiment of a fundus observation apparatus according to the present invention.

At first, the tomographic image forming part 232 forms a tomographic image representing the morphology of an optic disk based on the three-dimensional image V of the fundus Ef. According to this operational example, it is assumed that a horizontal tomographic image is formed for each of three xy slice surfaces W1, W2 and W3 having different depth positions (z coordinate positions) as shown in FIG. 5. Further, the number of tomographic images to be formed in Step 1 is not limited to three.

Figure 6:
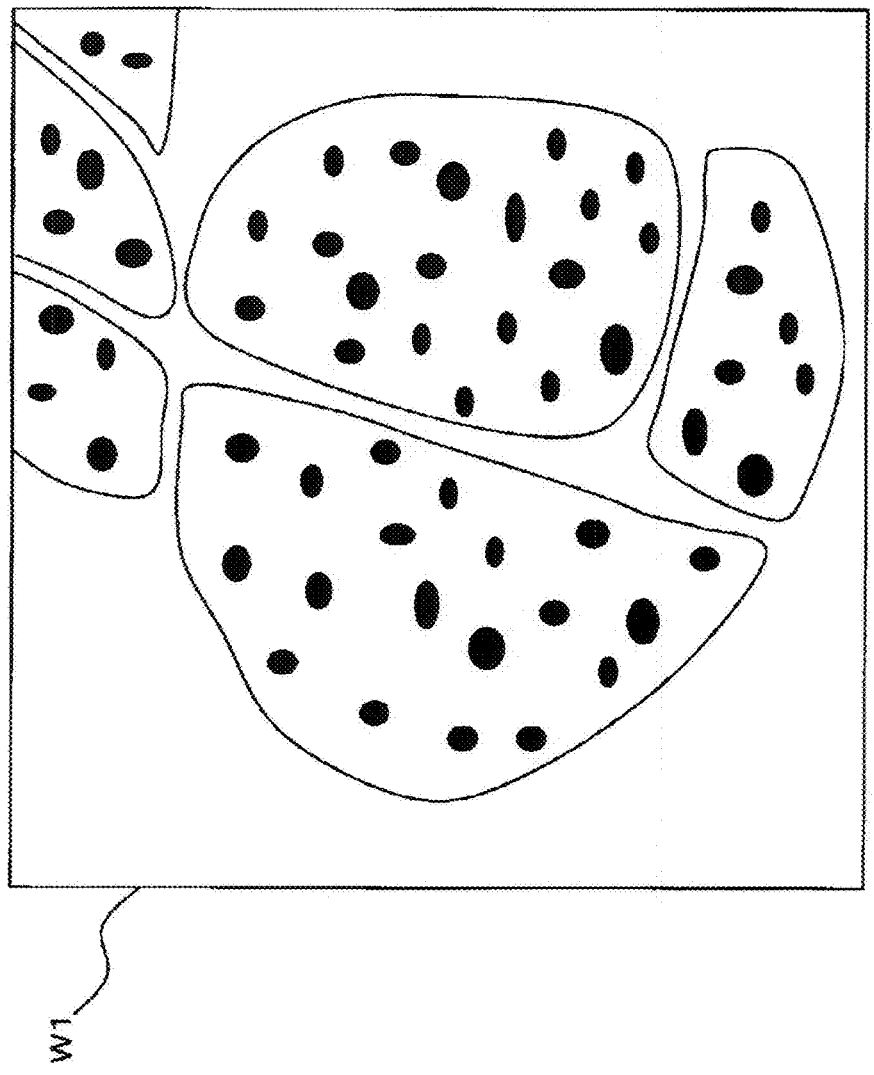
[FIG. 6] A schematic diagram for explaining processing executed by an embodiment of a fundus observation apparatus according to the present invention.

Each horizontal tomographic image is represented by the same code Wi (i=1 to 3) as that of the slice surface. The schematic appearance of a horizontal tomographic image W1 is shown in FIG. 6. The horizontal tomographic images W2 and W3 have similar appearance.

(S2)

Figure 7:
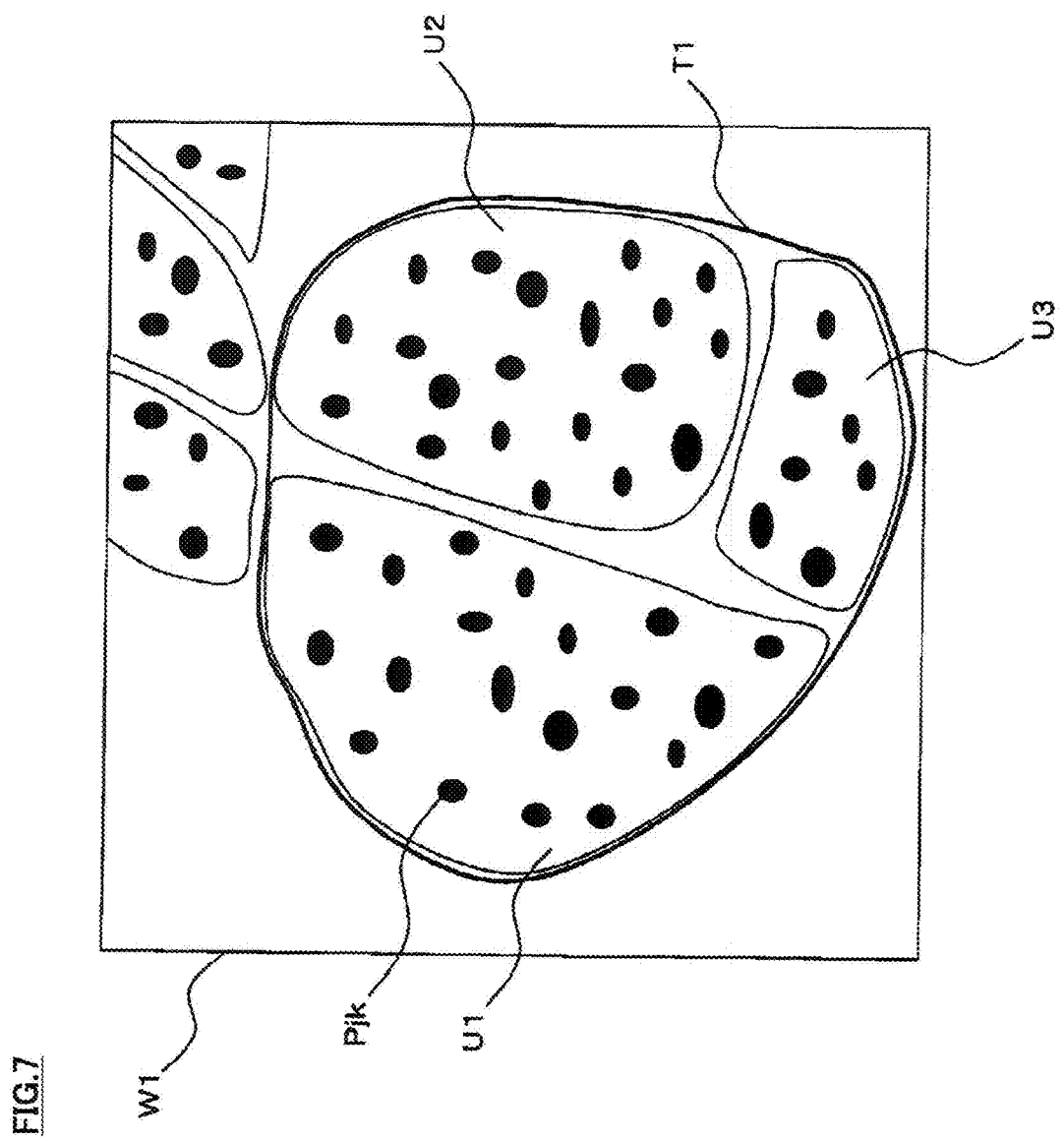
[FIG. 7] A schematic diagram for explaining processing executed by an embodiment of a fundus observation apparatus according to the present invention.

The cribrosa-lamina region specifying part 233 specifies the cribrosa-lamina region for each horizontal tomographic image Wi. Specifically, at first, the cribrosa-lamina region specifying part 233 specifies an optic disk region Ti and a blood-vessel region in each horizontal tomographic image Wi as shown in FIG. 7. Subsequently, the cribrosa-lamina region specifying part 233 specifies a cribrosa-lamina region Uj by removing the blood-vessel region from each optic disk region Ti. Sometimes the optic disk region is divided into multiple connected regions by the blood-vessel region. Accordingly, sometimes the cribrosa-lamina region is also configured by multiple connected regions Uj (in the example shown in FIG. 7, j=1 to 3).

(S3)

The hole region specifying part 234 analyses each horizontal tomographic image Wi to specify a hole region in the cribrosa-lamina region Uj. In FIG. 7, the specified hole regions are shown by a symbol Pjk (k=1 to L). Hereinafter, sometimes the hole region Pjk specified in each horizontal tomographic image Wi is shown by a symbol Pk collectively. As described above, multiple hole regions are generally specified.

Figure 8:
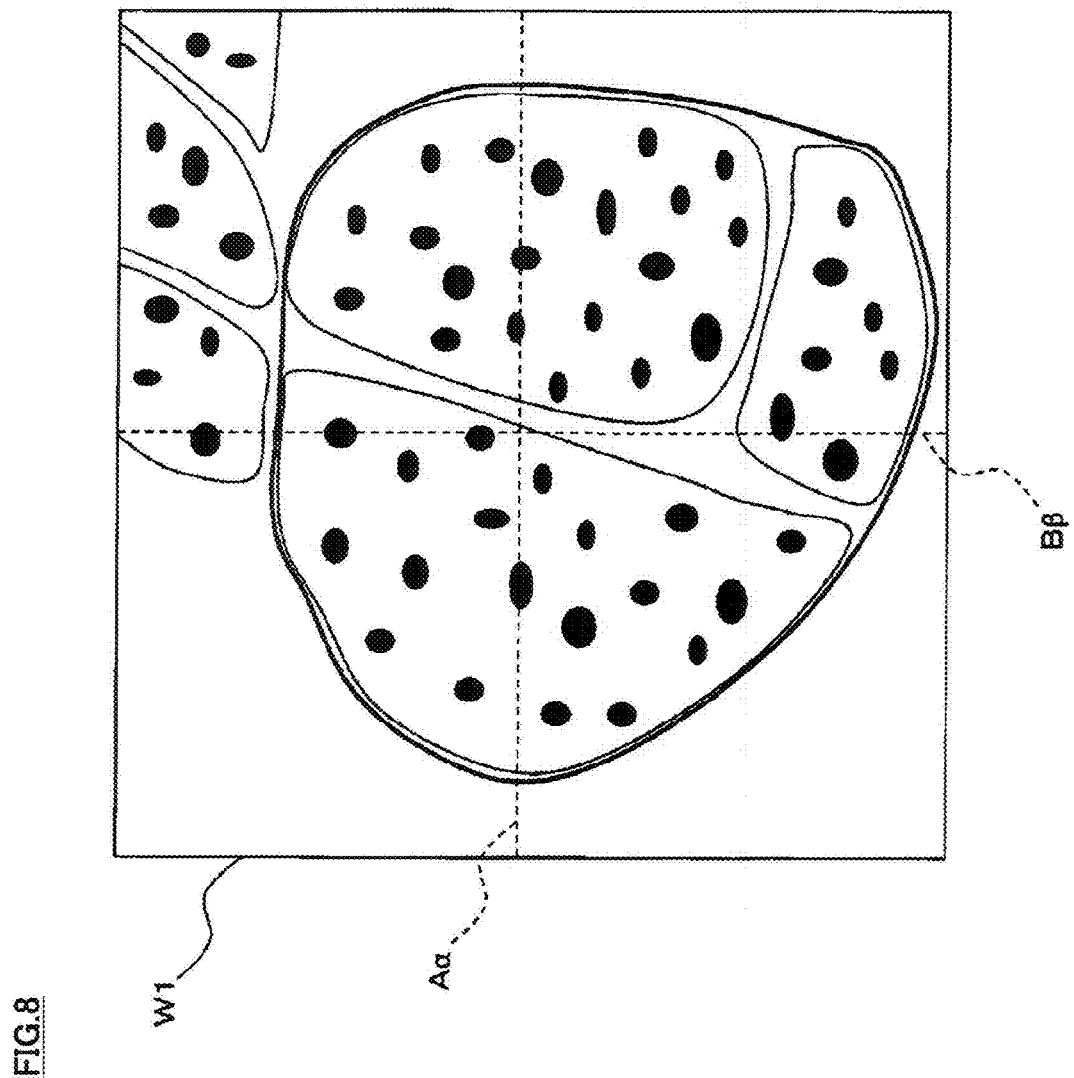
[FIG. 8] A schematic diagram for explaining processing executed by an embodiment of a fundus observation apparatus according to the present invention.

A specific example of the specification processing of the hole region will be described. At first, as shown in FIG. 8, the hole region specifying part 234 sets horizontal pixel lines Aα (α=1 to Nh: Nh is the number of pixels in the vertical direction) and vertical pixel lines Bβ (β=1 to Nv: Nv is the number of pixels in the horizontal direction).

Figure 9:
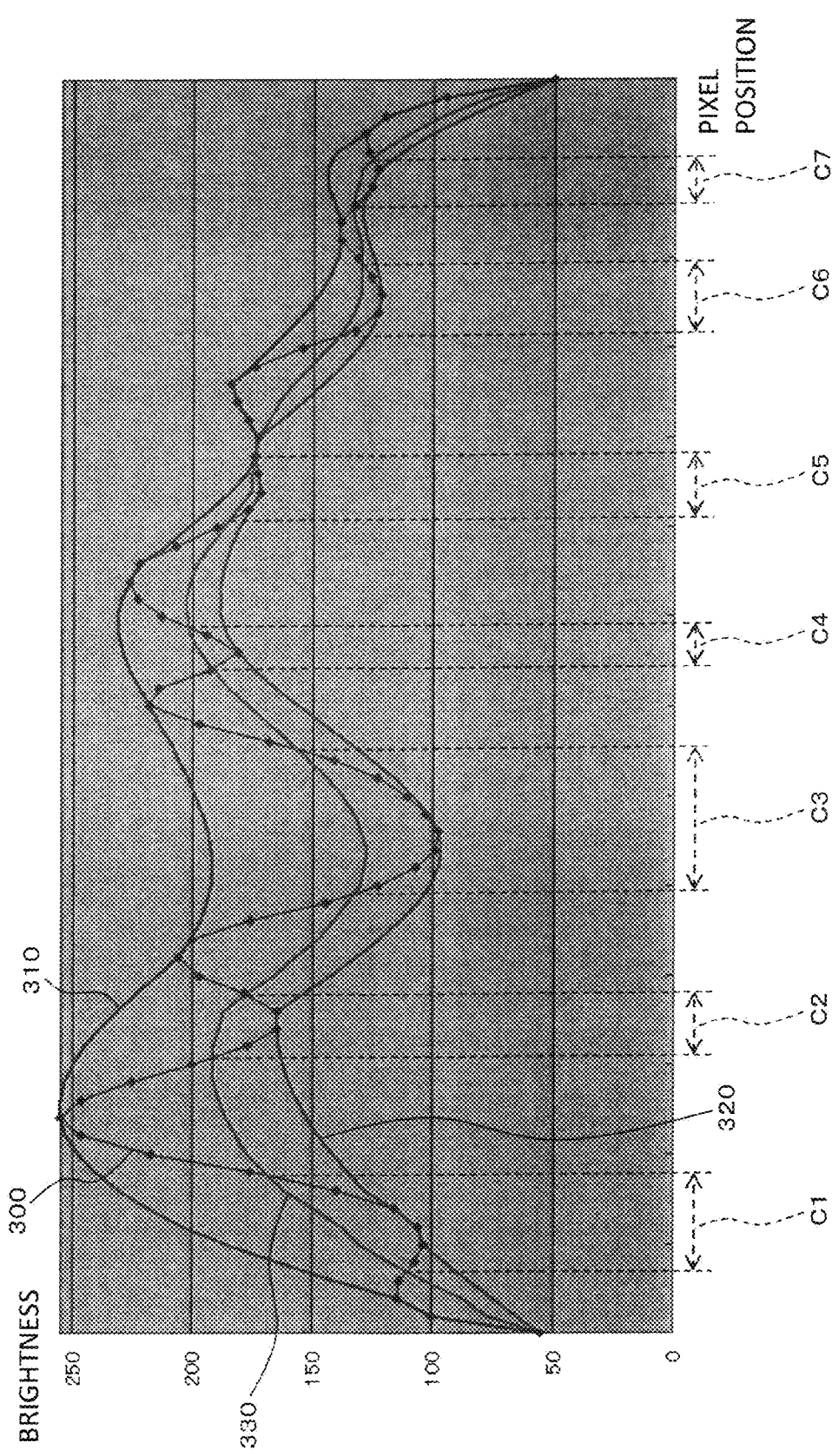
[FIG. 9] A graph for explaining processing executed by an embodiment of a fundus observation apparatus according to the present invention.

Next, the hole region specifying part 234 creates a brightness distribution graph for respective pixel lines Aα and Bβ. FIG. 9 shows a brightness distribution graph 300 based on the pixel line Aα. The brightness distribution graph 300 is obtained by plotting the position and brightness value of each pixel in the pixel line Aα and connecting the multiple plotted points by a curved line. This processing includes arbitrary processing for generating a curved line connecting discrete points such as a spline curve and a Bezier curve.

Subsequently, the hole region specifying part 234 obtains a maximal envelope 310 and a minimal envelope 320 of the brightness distribution graph 300. Further, the hole region specifying part 234 obtains a threshold graph 330 that internally divides the interval (space) between the maximal envelope 310 and the minimal envelope 320 in the coordinate axis representing the brightness value at a predetermined ratio (for example, 1:2).

Then, the hole region specifying part 234 specifies a pixel with a smaller brightness value than that of the threshold graph 330 to determine it as a candidate of the component pixel of the hole region. In the example shown in FIG. 9, the pixels included in ranges C1 to C7 on the coordinate axis indicating the pixel position are candidates for the component pixel of the hole region. In other words, the pixels included in each of the scopes C1 to C7 configure the above-described connected region. In this example, the hole region including seven connected regions is specified.

By performing the above processing for each of the pixel lines Aα and Bβ, a candidate of the component pixel of the hole region corresponding to each of the pixel lines Aα and Bβ is obtained. In this example, the processing for determining whether or not each pixel is a candidate for the component pixel of the hole region is carried out twice in the horizontal and vertical directions. The hole region specifying part 234 specifies the pixel that is determined as a candidate in both the horizontal and vertical directions to define image regions configured by the specified pixels as a hole region.

(S4)

The distribution information generating part 235 obtains the distribution of the hole regions Pk in the whole cribrosa-lamina regions Uj based on the cribrosa-lamina region Uj specified in Step 2 and the hole region Pk specified in Step 3. This distribution is based on the horizontal tomographic image and so is called "a horizontal distribution." Further, the distribution information generating part 235 obtains changes in the distribution of the hole region in the depth direction (a z-direction) based on these multiple (three in this example) horizontal distributions to define the obtained changes as the distribution information.

(S5)

The main controller 211 causes the display 240 to show the distribution information obtained in Step 4. At this time, the horizontal tomographic image Wi may be displayed together with the distribution information. In this case, it is possible to display, in respectively different display modes, the hole region Pk in the horizontal tomographic image Wi, image regions in the cribrosa-lamina region Uj other than the hole region Pk, and image regions in the horizontal tomographic image Wi other than the cribrosa-lamina region Uj. As an example of this, it is possible to make the display color and the display density of these image regions different.

The horizontal distribution calculated for each horizontal tomographic image Wi may be displayed. In addition, the graphs 300 to 330 obtained for each pixel line may be displayed.

[Actions and Effects]

The actions and effects of the fundus observation apparatus 1 as described above will be described.

The fundus observation apparatus 1 is operated so as to form a tomographic image (for example, the horizontal tomographic image Wi) based on the three-dimensional image V of the fundus Ef, specify the cribrosa-lamina region Uj by analyzing this tomographic image, specify the hole region Pk in this cribrosa-lamina region Uj, generate the distribution information representing the distribution of the hole region Pk in the cribrosa-lamina region Uj, and display this distribution information. Accordingly, it is possible to provide distribution information reflecting the status of the cribrosa lamina of the eye E as diagnostic material.

In addition, the fundus observation apparatus 1 can display the horizontal tomographic image Wi together with the distribution information. At this time, it is possible to display, in respectively different display modes, the hole region Pk, image regions in the cribrosa-lamina region Uj other than the hole region Pk, and image regions in the horizontal tomographic image Wi other than the cribrosa-lamina region Uj. Thereby, it is possible for the user to visually recognize the morphology of the fundus Ef in the slice surface depicted by the horizontal tomographic image Wi such as the morphology and the distribution status of the hole region Pk, and further, the morphology of the cribrosa-lamina region Uj or the like.

In addition, the fundus observation apparatus 1 can form multiple horizontal tomographic images Wi with different depth positions, specify the cribrosa-lamina region Uj and the hole region Pk for each horizontal tomographic image Wi, obtain the horizontal distribution of the hole region Pk in each cribrosa-lamina region Uj, and obtain changes in the distribution of the hole region Pk in the depth direction to define the obtained changes as the distribution information. Thereby, it is possible to grasp the three-dimensional distribution status of the hole region in the fundus Ef.

In addition, in the processing for specifying the cribrosa-lamina region Uj, the fundus observation apparatus 1 may specify the optic disk region Ti and the blood-vessel region in the horizontal tomographic image Wi, and define the region obtained by removing the blood-vessel region from the optic disk region Ti as the cribrosa-lamina region. Thereby, it is possible to obtain the distribution information without being influenced by the blood vessels of the fundus.

In addition, the fundus observation apparatus 1 may specify the hole region Pk by creating a brightness distribution graph 300, a maximal envelope 310, a minimal envelope 320, and a threshold graph 330. This makes it possible to preferably carry out the processing for specifying the component pixel of the hole region Pk.

[Other Embodiments]

Other embodiments of the fundus observation apparatus will be described. In the following embodiments, the configuration of the apparatus is similar to that of the above-described embodiment.

In the case of generating distribution information representing changes of the distribution in the depth direction, the fundus observation apparatus 1 can form a new three-dimensional image based on the horizontal tomographic images Wi. This processing is carried out by the three-dimensional image forming part 231. This three-dimensional image forming part 231 is an example of "the three-dimensional image forming part" of the present invention. In this embodiment, it is necessary to form sufficient horizontal tomographic images to form a three-dimensional image.

According to this embodiment, it is possible to obtain a three-dimensional image depicting the three-dimensional distribution of the optic disk region Ti, the cribrosa-lamina region Uj, and the hole region Pk. In addition, by carrying out image processing such as the above-described smoothing processing, processing to enlarge a dynamic range, and unsharp masking processing, it is possible to improve the image quality of a new three-dimensional image. In addition, by appropriately setting the opacity of the three-dimensional image and performing rendering, it is possible to display the distribution status of the cribrosa-lamina region and the hole region in an easily visually understandable way.

Further, it is possible to employ a configuration in which the tomographic image forming part 232 forms a vertical tomographic image along the depth direction based on the new three-dimensional image, and the display 240 displays this vertical tomographic image. This enables to provide additional diagnostic material since the vertical tomographic image can be observed in addition to the horizontal tomographic image.

In the case of displaying the vertical tomographic image, it is possible to change the display mode (the display color and the display density or the like) of the hole region Pk based on the distribution information. This allows the user to visually recognize the distribution status of the hole region Pk in the depth direction.

Another embodiment will be described. At first, the tomographic image forming part 232 forms a vertical tomographic image along the depth direction based on the three-dimensional image V. Next, the cribrosa-lamina region specifying part 233 specifies the cribrosa-lamina region in this vertical tomographic image. Further, the hole region specifying part 234 specifies the hole region in this vertical tomographic image. Then, it is possible to obtain the vertical distribution of the hole region in the cribrosa-lamina region based on the specifying results of the cribrosa-lamina region and the hole region by the distribution information generating part 235, the obtained vertical distribution can be made into distribution information. These respective processes can be carried out as well as the above-described embodiment(s). According to this embodiment, it is possible to provide the vertical tomographic image and the distribution information as diagnostic material.

In the above embodiment, the position of the reference mirror 114 is changed so as to change an optical path length difference between the optical path of the signal light LS and the optical path of the reference light LR. However, a method for changing the optical path length difference is not limited thereto. For example, it is possible to change the optical path length difference by moving the retinal camera unit 2 and the OCT unit 100 with respect to the eye E to change the optical path length of the signal light LS. Moreover, in a case that an object is not a living site or the like, it is also effective to change the optical path length difference by moving the object in the depth direction (z-direction).

The computer program used in the above embodiments can be stored in any kind of recording medium that can be read by a computer. As this recording medium, for example, an optical disk, a magneto-optic disk (CD-ROM, DVD-RAM, DVD-ROM, MO, and so on), and a magnetic storage (a hard disk, a floppy Disk™, ZIP, and so on) can be used. Moreover, it is possible to store into a storing device such as a hard disk drive and a memory.

In addition, it is possible to transmit/receive this program through a network such as internet or LAN etc.

The configuration described above is merely one example for favorably implementing the present invention. Therefore, it is possible to properly make arbitrary modification within the scope of the present invention.

EXPLANATION OF SYMBOLS 1 fundus observation apparatus
43, 44 Galvano mirror
100 OCT unit
200 arithmetic and control unit
210 controller
211 main controller
212 storage
220 image forming part
230 image processor
231 three-dimensional image forming part
232 tomographic image forming part
233 cribrosa-lamina region specifying part
234 hole specifying part
235 distribution information generating part
240 display
E eye
Ef fundus

The invention claimed is:

1. A fundus image processing apparatus for receiving and processing three-dimensional image representing the morphology of a region of a fundus including the optic disk of an eye, comprising:
a tomographic image forming part that forms a tomographic image representing the morphology of the optic disk based on the three-dimensional image;
a first specifying part that analyzes the tomographic image and specifies a cribrosa-lamina region in the tomographic image;
a second specifying part that analyzes the tomographic image and specifies a hole region in the cribrosa-lamina region;
a generating part that generates distribution information representing the distribution, in the cribrosa-lamina region, of the hole region that are specified by the second specifying part; and
a display that displays the distribution information,
wherein the tomographic image comprises an image having multiple pixels representing brightness values arrayed in a matrix, and
the second specifying part creates a first graph to relate the position of the pixel in each pixel line in the vertical direction and/or the horizontal direction in the tomographic image with the brightness value, obtains a maximal envelope connecting the local maximums of the first graph and a minimal envelope connecting the local minimums of the first graph, obtains a second graph that internally divides the interval between the maximal envelope and the minimal envelope in the direction of a coordinate axis representing the brightness value of the first graph at a predetermined ratio, and specifies a pixel with a smaller brightness value than that of the second graph as a pixel of the hole region.

2. The fundus image processing apparatus according to claim 1, wherein the distribution information includes at least one of a statistical value based on the sizes of multiple connected regions included in the hole region and the area ratio between the hole region and the cribrosa-lamina region.

3. The fundus image processing apparatus according to claim 1, wherein the display shows the tomographic image so that the hole region, an image region in the cribrosa-lamina region other than the hole region, and an image region in the tomographic image other than the cribrosa-lamina region are shown in respectively different display modes.

4. A fundus image processing apparatus for receiving and processing a three-dimensional image representing the morphology of a region of a fundus including the optic disk of an eye, comprising:

tomographic image forming part that forms a tomographic image representing the morphology of the optic disk based on the three-dimensional image, wherein the tomographic image forming part forms, as the tomographic image, multiple horizontal tomographic images that are perpendicular to the depth direction of the optic disk and have different depth positions;

a first specifying part that analyzes the tomographic image and specifies a cribrosa-lamina region region in the tomographic image, wherein the first specifying part specifies the cribrosa-lamina region for each of the multiple horizontal tomographic images;

a second specifying part that analyzes the tomographic image and specifies a hole region in the cribrosa-lamina region, wherein the second specifying part specifies the hole region for each of the multiple horizontal tomographic images;

a generating part that generates distribution information representing the distribution, in the cribrosa-lamina region, of the hole region that are specified by the second specifying part, wherein the generating part obtains a horizontal distribution of the hole region in the cribrosa-lamina region at each of the different depth positions based on the specifying results of the cribrosa-lamina region and the specifying results of the hole region, and further obtains, as the distribution information, changes of the distribution of the hole region in the depth direction based on the horizontal distributions at the different depth positions;

a three-dimensional image forming part that forms a new three-dimensional image based on the multiple horizontal tomographic images from which the distribution information representing the changes of the distribution is obtained, wherein the tomographic image forming part forms a vertical tomographic image along the depth direction based on the new three-dimensional image; and a display that displays the distribution formation, wherein the display shows the vertical tomographic image while changing the display mode of the hole region based on the distribution information.

5. The fundus image processing apparatus according to claim 1, wherein the tomographic image forming part forms a vertical tomographic image along the depth direction of the optic disk based on the three-dimensional image;

the first specifying part specifies the cribrosa-lamina region in the vertical tomographic image;

the second specifying part specifies the hole region in the vertical tomographic image;

the generating part obtains, as the distribution information, the vertical distribution of the hole region in the cribrosa-lamina region based on the specifying result of the cribrosa-lamina region and the specifying result of the hole region.

6. The fundus image processing apparatus according to claim 1, wherein the first specifying part specifies a disk region corresponding to the optic disk and a blood-vessel region corresponding to a blood vessel in the tomographic image based on a pixel value of the tomographic image, and specifies the region obtained by removing the blood-vessel region from the disk region as the cribrosa-lamina region.

7. The fundus image processing apparatus according to claim 1, wherein the tomographic image forming part forms the tomographic image representing the morphology of the optic disk in a depth where the lamina cribrosa is located.

8. The fundus observation apparatus according to claim 4, wherein the tomographic image forming part forms the tomographic image representing the morphology of the optic disk in a depth where the lamina cribrosa is located.

* * * * *

UNITED STATES PATENT AND TRADEMARK OFFICE
CERTIFICATE OF CORRECTION

| | | |
|---|---|---|
| PATENT NO. | : 9,275,283 B2 | Page 1 of 1 |
| APPLICATION NO. | : 13/806326 | |
| DATED | : March 1, 2016 | |
| INVENTOR(S) | : Masahiro Shibutani | |

It is certified that error appears in the above-identified patent and that said Letters Patent is hereby corrected as shown below:

In the specification,

Column 10, line 23, "The control system of the fundus observation apparatus has"
should read --The control system of the fundus observation apparatus 1 has--

In the claims,

Column 21, claim 4, line 23, "tomographic image forming part that forms a tomographic"
should read --a tomographic image forming part that forms a tomographic--

Column 21, claim 4, line 31, "and specifies a cribrosa-lamina region region in the"
should read --and specifies a cribrosa-lamina region in the--

Signed and Sealed this
Seventh Day of June, 2016

Michelle K. Lee
*Director of the United States Patent and Trademark Office*